United States Patent
Lee et al.

(10) Patent No.: US 8,412,344 B2
(45) Date of Patent: Apr. 2, 2013

(54) DEEP BRAIN STIMULATION DEVICE HAVING WIRELESS POWER FEEDING BY MAGNETIC INDUCTION

(75) Inventors: Uhn Lee, Incheon (KR); Sang Hyouk Choi, Poquoson, VA (US); Yeon Joon Park, Yorktown, VA (US)

(73) Assignee: Gachon University of Medicine # Science Industry-Academic Cooperation Foundation, Incheon (KR)

( * ) Notice: Subject to any disclaimer, the term of this patent is extended or adjusted under 35 U.S.C. 154(b) by 328 days.

(21) Appl. No.: 12/600,032

(22) PCT Filed: May 14, 2008

(86) PCT No.: PCT/KR2008/002664
§ 371 (c)(1),
(2), (4) Date: Jun. 23, 2010

(87) PCT Pub. No.: WO2008/014024
PCT Pub. Date: Nov. 20, 2008

(65) Prior Publication Data
US 2011/0046693 A1     Feb. 24, 2011

(30) Foreign Application Priority Data
May 14, 2007 (KR) .................. 10-2007-0046408

(51) Int. Cl.
*A61N 1/08* (2006.01)
(52) U.S. Cl. ...................................................... 607/61
(58) Field of Classification Search .............. 607/45, 607/46, 48, 49, 61
See application file for complete search history.

(56) References Cited

U.S. PATENT DOCUMENTS

| | | | |
|---|---|---|---|
| 6,427,086 B1 | 7/2002 | Fischell et al. | |
| 7,013,177 B1 | 3/2006 | Whitehurst et al. | |
| 2002/0002390 A1* | 1/2002 | Fischell et al. | 607/45 |
| 2005/0187488 A1 | 8/2005 | Wolf | |
| 2005/0228209 A1* | 10/2005 | Schneider et al. | 600/13 |
| 2005/0283202 A1 | 12/2005 | Gellman | |
| 2006/0184209 A1 | 8/2006 | John et al. | |
| 2006/0212097 A1 | 9/2006 | Varadan et al. | |

OTHER PUBLICATIONS

International Search Report of International Application No. PCT/KR2008/002664, filed May 14, 2008, International Publication No. Wo 2008/140243 A3, published Nov. 20, 2008, of Gachon University of Medicine # Science Industry-Academic Cooperation Foundation, of inventors Uhn Lee et al., for a Deep Brain Stimulation Device Having Wireless Power Feeding by Magnetic Induction.

* cited by examiner

*Primary Examiner* — Tammie K Heller
(74) *Attorney, Agent, or Firm* — Patent Office of Dr. Chung Park

(57) ABSTRACT

Provided is a deep brain stimulation (DBS) device having power wirelessly fed by magnetic induction. A rotating magnetic field is formed using a rotating magnetic field disk installed inside a hat of a patient. The rotating magnetic field generates induced power using an induction coil plate fixed underneath a scalp of the patient to drive electrodes implanted into a brain of the patient so as to correct abnormal motor and sensory functions of the patient using power wirelessly fed from an external device into the electrodes. The DBS device includes: a hat module installed inside a hat of the patient to generate a rotating magnetic field; and an implantation module implanted through a skull under a scalp to contact a nervous system of the patient and combined with the rotating magnetic field of the hat module to stimulate the cerebral nerve using induced power generated by the magnetic induction.

5 Claims, 2 Drawing Sheets

[Fig. 1] PRIOR ART
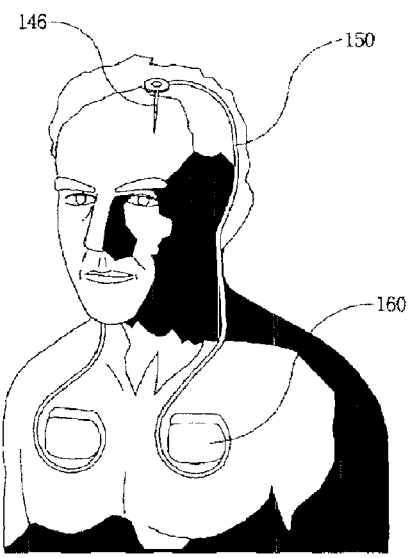
[Fig. 2]
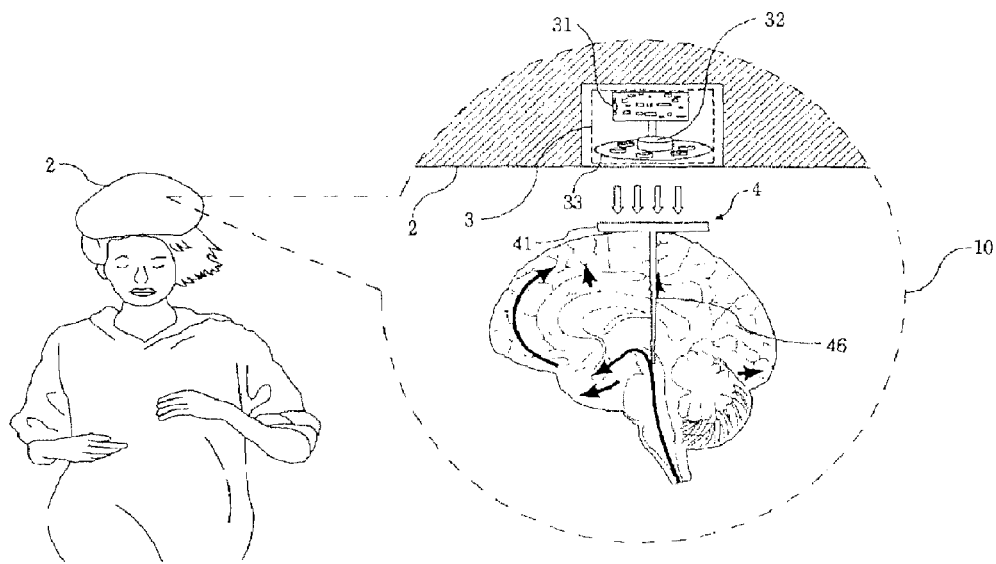

[Fig. 3]
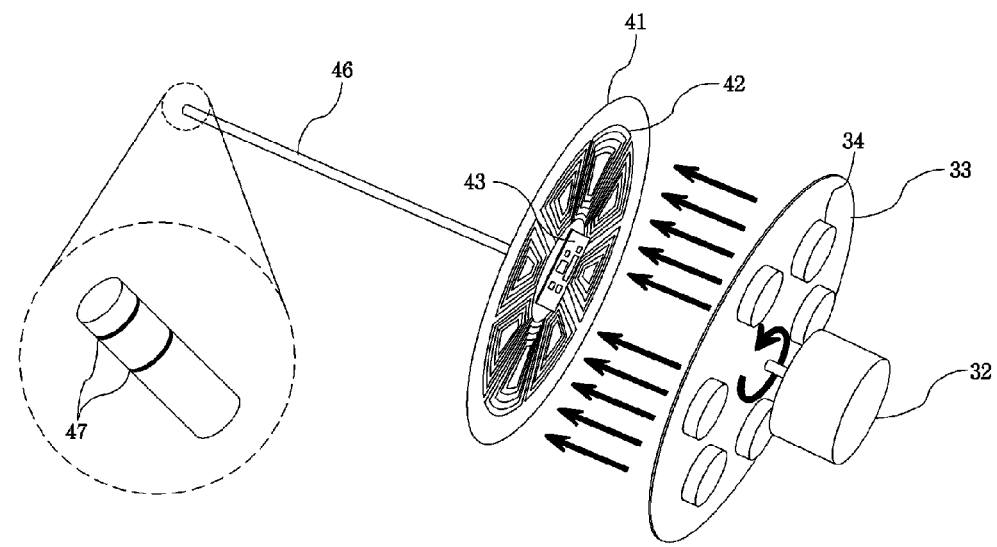
[Fig. 4]
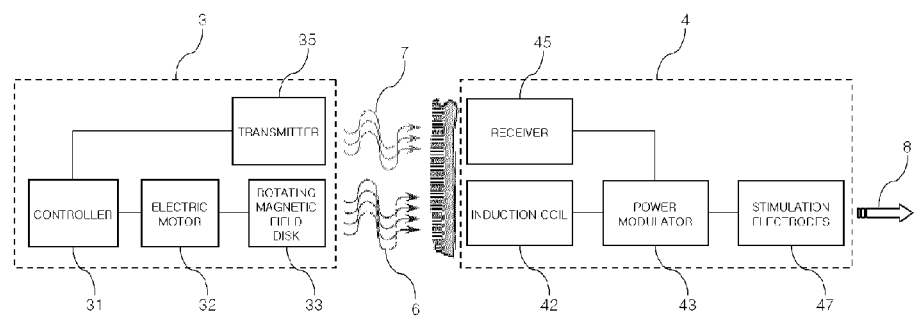

DEEP BRAIN STIMULATION DEVICE HAVING WIRELESS POWER FEEDING BY MAGNETIC INDUCTION

CROSS REFERENCES TO RELATED APPLICATIONS

This application is a national phase application based upon priority International PCT Patent Application No. PCT/KR2008/002664 filed 14 May 2008, International Publication No. WO/2008/140243 A3 published 20 Nov. 2008, which is based upon priority Korean Patent Application No. 10-2007-0046408 filed 14 May 2007.

BACKGROUND OF THE INVENTION

1. Technical Field

The present invention relates to a deep brain stimulation (DBS) device having power wirelessly fed by a magnetic induction, and more particularly, to a DBS device which forms a rotating magnetic field by a rotating magnetic field disk installed inside a hat put on a patient and generates induced power by an induction coil plate fixed underneath a scalp of the patient so that the induced power is combined with the rotating magnetic field to drive electrodes implanted into a brain of the patient so as to correct abnormal motor and sensory functions of the patient using power wirelessly fed from an outside into a body of the patient.

2. Background Art

People are exposed to accidents or diseases that may result in them losing the ability to function or move. There are limits to curing such patients in medical science. Medical and biological engineering in which an engineering field is grafted into a medical field has been developed in order to overcome the above-described limits. Thus, many areas of a health management system have been changed.

For example, cardiac pacemakers and defibrillators have saved lives of hundreds of people and cured heart diseases. Also, surgeons implant deep brain stimulation (DBS) devices into brains of patients to control abnormal brain functions of the patients using techniques of cardiac pacemakers.

Abnormal physical actions or mental disorders derive from abnormal functions of brains such as a Parkinson's disease or an obsessive-compulsive disorder (OCD). The Parkinson's disease is a chronic degenerative disease whose main symptoms are shivering of hands and feet, slow actions, and hardening of muscles. In other words, the Parkinson's disease is a mental disease by which a person with an OCD avoids going out due to a fear of contaminations from things that the person contacts.

Neurosurgeons use DBS devices to cure health problems such as the Parkinson's disease, an OCD, and hypochondria. A curing method using a DBS device is an only surgical method for curing an OCD and is effective in curing the Parkinson's disease. This curing method requires a process of implanting an electrode, which inhibits or stimulates a predetermined part of a cerebral nerve, into a deep part of a brain in order to normalize a function of the brain of a patient.

Operations using DBS devices have been performed since Alim-Louis Benabid in the Grenoble University Hospital of France reported on 80 or more Parkinson's disease patients in 1993. Thus, about thirty thousand similar operations have been very successfully performed throughout the world. Such a DBS device applies current pulses to a cerebral nerve through electrodes, which are implanted into an accurate position of the cerebral nerve, in order to stop shivering, which is a main symptom of a disease, and relax stooped muscles.

DBS devices contribute to controls of extant diseases. However, when a DBS device uses an electric wire in a human body to supply power, transmit data, and make a program, a plurality of problems occur.

FIG. 1 illustrates a conventional DBS device which is implanted into a human body. Referring to FIG. 1, the conventional DBS device includes an electrode needle 146 and a power supply unit 160. The electrode needle 146 is implanted into a cerebral nerve to provide an electric stimulation to the cerebral nerve so as to restore an abnormal function of a brain. The power supply unit 160 is connected to the electrode needle 146 through an electric wire 150 to feed power to the electrode needle 146.

The conventional DBS device having the above-described structure sews the power supply unit 160 having a power source such as a battery into abdomen or thorax to be turned on or off by remote control using a skin. Thus, the DBS device is clinically simply used. However, the DBS device provides hard inconvenience to a patient. Also, if the electric wire 550 installed underneath the skin of the patient short-circuits or power of the battery installed in the abdomen or thorax is consumed, a surgical operation is repeatedly performed to replace or repair a corresponding part.

BRIEF SUMMARY OF THE INVENTION

Disclosure of Invention Technical Problem

The present invention provides a deep brain stimulation (DBS) device which electrically stimulates a cerebral nerve of a patient using power, which is wirelessly fed from an outside into a body of the patient.

Advantageous Effects

A deep brain stimulation (DBS) device having power wirelessly fed by a magnetic induction according to the present invention normalizes an abnormal cerebral nervous system of a patient and strengthens weakened functions of the cerebral nervous system. Also, the DBS device does not include an additional power feeding device which is implanted into a body of the patient and thus does not require an additional operation for replacing a power source and an electric wire. The DBS device permanently operates due to an only one-time performance of an operation for implanting the DBS device. Thus, maintenance cost of the DBS device is considerably saved, pains of a patient causes by repeated operations are relieved.

A more detailed explanation of the invention is provided in the following detailed description and appended claims taken in conjunction with the accompanying drawings.

BRIEF DESCRIPTION OF THE DRAWINGS

FIG. 1 illustrates a conventional deep brain stimulation (DBS) device which is implanted into a human body.

FIG. 2 illustrates a DBS device having power wirelessly fed by a magnetic induction according to an embodiment of the present invention.

FIG. 3 is a perspective view of parts of a wireless power feeding module using an induction coil, shown in FIG. 2.

FIG. 4 is a block diagram of the DBS device of FIG. 2.

DETAILED DESCRIPTION OF THE INVENTION

The following is a detailed description and explanation of the preferred embodiments of the invention and best mode for practicing the invention.

Best Mode for Carrying out the Invention

According to an aspect of the present invention, there is provided a deep brain stimulation (DBS) device including: a hat module which is installed inside a hat put on a head of the patient to generate a rotating magnetic field; and an implantation module which is implanted through a skull under a scalp to contact a nervous system of the patient and combined with the rotating magnetic field of the hat module to stimulate the cerebral nerve using induced power generated by the magnetic induction.

Mode for the Invention

Exemplary embodiments of the present invention will now be described in detail with reference to the attached drawings.

FIG. 2 illustrates a DBS device having power wirelessly fed by a magnetic induction according to an embodiment of the present invention. Referring to FIG. 2, a DBS device 10 of the present embodiment includes an implantation module 4 and a hat module 3. The implantation module 4 is implanted into a head of a patient. The hat module 3 is installed inside a hat 2 put on the head of the patient to generate a rotating magnetic field so as to wirelessly feed power which is to be used by the implantation module 4.

The implantation module 4 includes a stimulation pin 46 and an induction coil plate 41. The stimulation pin 46 is implanted through a skull under a scalp to contact a deep cerebral nerve so as to provide an electric stimulation to the deep cerebral nerve of the patient. The induction coil plate 41 generates induced power for driving the stimulation pin 46.

Here, the induction coil plate 41 is combined into the skull under the scalp using screws, and the stimulation pin 46 is connected to a center of a lower surface of the induction coil plate 41 to be fixed into a position in which a nervous stimulation is to be provided.

The hat module 3 includes a rotating magnetic field disk 33, a small-sized electric motor 32, and a controller 31. The rotating magnetic field disk 33 generates a rotating magnetic field toward the induction coil plate 41 of the implantation module 4 in order to generate power which is to be used to drive the implantation module 4. The small sized electric motor 32 rotates the rotating magnetic field disk 33, and the controller 31 controls the small-sized electric motor 32.

The rotating magnetic field disk 33 of the hat module 3 and the induction coil plate 41 of the implantation module 4 constitute a wireless power feeding module to wirelessly feed power through a magnetic induction generated between the rotating magnetic field disk 33 and the induction coil plate 41. Thus, the DBS device 10 self-feeds power for driving the stimulation pin 46 without installing an additional power source into the body of the patient.

FIG. 3 is a perspective view of parts of the wireless power feeding module using an induction coil, shown in FIG. 2. Wireless power feeding between the implantation module 4 and the hat module 3 is shown in FIG. 3.

The wireless power feeding uses induced power. In other words, the wireless power feeding is a method of generating induced power by a relative motion between the rotating magnetic field disk 33 of the hat module 3 and the induction coil plate 41 of the implantation module 4.

As shown in FIG. 3, a plurality of small-sized magnets 34 are attached on a surface of the rotating magnetic field disk 33 to be disposed at equal intervals along a circumference of the rotating magnetic field disk 33. A minute induction coil 42 is formed of a metal line in a predetermined pattern on the induction coil plate 41 having a thin film shape so as to be disposed around a power modulator 43 which is positioned in the center of the induction coil plate 41. If the rotating magnetic field disk 33 of the hat module 3 rotates based on an axis, magnetic force lines generated from the smallsized magnets 34 rotate. Thus, induced power is generated from the induction coil plate 41 which is fixed underneath the scalp. The induced power is transmitted to the power modulator 43 connected to the minute induction coil 42 to be used to drive the stimulation pin 46 which is to stimulate neurons in the brain.

Power necessary for stimulating a deep brain may be pulse waves which have a minimum frequency of 200 Hz, a pulse width between 60 µsec and 500 µsec, and a magnitude between 0V and ±10V.

Therefore, the power modulator 43 modulates direct current (DC) power, which is generated by the magnetic induction generated by the minute induction coil 42, into pulse waves which have a magnitude between 0V and ±10V, a frequency of 200 Hz, and a pulse width between 60 µsec and 500 µsec. Next, the power modulator 43 feeds the pulse waves to the stimulation pin 46.

The stimulation pin 46 is an only part which is buried into the brain to stimulate the deep brain. Also, the induction coil plate 41, which is formed of a minute thin film and positioned between the scalp and the skull, is combined with a magnetic field which rotates to generate power required for performing functions of the stimulation pin 46. Therefore, the induction coil plate 41 transforms kinetic energy into electric energy which is to be used by the implantation module 4 and feeds the electric energy to the implantation module so as to wirelessly feed power from the hat module 3 positioned outside the body of the patient to the implantation module 4 implanted into the body of the patient. Here, the kinetic energy is generated by the small-sized electric motor 32 of the hat module 3 using the rotating magnetic field disk 33 and the induction coil plate 41 which are opposite to each other so that an air gap is formed between the rotating magnetic field disk 33 and the induction coil plate 41.

The stimulation pin 46 is implanted into a minute path of an activity cerebral cortex so that a lower end of the stimulation pin 46 contacts a deep cerebral nerve. A body of the stimulation pin 46 may be formed of a material which does not react to and reject fluid in a human body. In particular, the body of the stimulation pin 46 may be formed of a polymer or ceramic material which is physiologically well adapted to the human body.

A plurality of stimulation electrodes 47 are installed at the lower end of the stimulation pin 46 to transmit a voltage for stimulating the cerebral nerve. An insulating material is coated from upper surfaces of the stimulation electrodes 47 up to a tip area in order to prevent an electric leakage to the human body. Here, the plurality of stimulation electrodes 47 installed in the stimulation pin 46 are formed of insulation coated gold lines.

FIG. 4 is a block diagram of the DBS device 10 of FIG. 2.

A whole structure and operation of the DBS device 10 will now be described in detail with reference to FIG. 4.

As previously described, the DBS device 100 includes the hat module 3 which is installed inside the hat 2 put on the patient and the implantation module 4 which is implanted into the brain of the patient.

The hat module 3 includes the small-sized electric motor 32, the rotating magnetic field disk 33, a transmitter 35, and the controller 31. The controller 31 rotates the small-sized electric motor 32 at a constant speed and transmits a nerve stimulation command signal 7 to the implantation module 4 through the transmitter 35.

A central portion of the rotating magnetic field disk 33 is connected to a shaft of the small-sized electric motor 32 so that the rotating magnetic field disk 33 rotates with driving of the small-sized electric motor 32. Thus, the plurality of small-sized magnets 34, which are attached on an upper surface of the rotating magnetic field disk 33 to form a concentric circle based on the axis, rotate so as to rotate a magnetic field 6 formed toward the implantation module 4.

A power feeding unit (not shown) is installed to be connected to the controller 31 and the small-sized electric motor 32 so as to feed power to the whole circuit and the smallsized electric motor 32 of the hat module 3.

The implantation module 4 implanted into the brain includes the stimulation pin 46, the induction coil plate 41, a receiver 45, and the power modulator 43. The simulation pin 46 includes the stimulation electrodes 47, and the induction coil plate 41 wirelessly receives energy and transforms the energy into power. The receiver 45 receives a command signal from the transmitter 35 of the hat module 3. The power modulator 43 modulates the power generated by the induction coil plate 41 into power which is to be used by the whole circuit and the stimulation pin 46.

Here, the stimulation electrodes 47 transmit a stimulation signal 8 to the cerebral nerve to inhibit an abnormal motor or sensory function of the patient.

Accordingly, the rotations of the small-sized magnets 34 of the hat module 3 generate induced electricity in the minute conduction coil 42 of the induction coil plate 41 implanted underneath the scalp. Next, the power modulator 43 modulates the induced electricity into DC current having a predetermined voltage necessary for driving a system and feeds the DC current to the whole circuit and the stimulation electrodes 47. In other words, power is not directly transmitted by wire but is generated by the minute induction coil 42 which is combined with the magnetic field which continuously varies, passing through a thickness of the skin. The generated induced power is modulated into the DC power to drive the implantation module 4 including the stimulation pin 46. Here, as described above, the power fed to the stimulation pin 46 has a pulse waveform required for stimulating a deep brain stimulation.

Here, the hat module 3 includes a switch (not shown) which is connected to the controller 31 and turns on and/or off a cerebral nerve stimulation function of the implantation module 4. Thus, the controller 31 drives the small-sized electric motor 32 and transmits a cerebral nerve stimulation command signal to the receiver 45 of the implantation module 4 through the transmitter 35 according to an operation of the switch. Next, the controller 31 operates the power modulator 43 according to the cerebra nerve stimulation command signal to feed pulse power to the stimulation electrodes 47 so as to simulate the cerebral nerve.

If the induced power is generated by an interaction between the rotating magnetic field disk 33 and the induction coil 42 generated by the driving of the small-sized electric motor 32 without installing the transmitter 35 and the receiver 45, the power modulator 43 may immediately operate to feed the pulse power to the stimulation electrodes 47.

A patient who is implanted with the DBS device 10 having the above-described structure is able to freely move with the hat 2 adjacent to the minute induction coil 42 implanted into a brain of the patient. If an abnormal symptom, such as hand shivering of a Parkinson's disease patient, occurs in a cerebral nerve of the patient, the patient or another person may operate the switch of the hat 2 to combine rotating magnetic force lines generated from the rotating magnetic field disk 33 of the hat module 3 with the induction coil 42 implanted underneath the scalp in order to generate induced power. Next, the stimulation pin 46 may be operated by the induced power so as to solve an abnormal function of a brain of the patient.

As described above, a DBS device having power wirelessly fed by a magnetic in duction according to the present invention wirelessly transmits power compared to a conventional DBS device which is sewed into abdomen or thorax to be turned on and/or off by remote controls through a skin. Thus, the DBS device does not require a surgical operation which is performed to replace a battery and other elements implanted into a body of a patient.

While the present invention has been particularly shown and described with reference to exemplary embodiments thereof, it will be understood by those of ordinary skill in the art that various changes in form and details may be made therein without departing from the spirit and scope of the present invention as defined by the following claims.

Industrial Applicability

A DBS device having power wirelessly fed by a magnetic induction according to the present invention normalizes functions of a patient having an abnormal cerebral nervous system and strengthens weakened functions of the cerebral nervous system. Also, the DBS device permanently operates through only a one-time operation.

Although embodiments of the invention have been shown and described, it is to be understood that various modifications, substitutions, and rearrangements of parts, components, and/or process (method) steps, as well as other uses of the DBS device, can be made by those skilled in the art without departing from the novel spirit and scope of this invention.

What is claimed is:

1. A deep brain stimulation (DBS) device having power wirelessly fed by a magnetic induction to stimulate a cerebral nerve of a patient having abnormal motor and sensory functions so as to normalize functions of a brain of the patient, the DBS device comprising:
    a hat module configured for placement over a head of the patient and to generate a rotating magnetic field;
    an implantation module configured to be implanted through a skull under a scalp of the patient to thereby contact a nervous system of the patient, and, when combined with the rotating magnetic field, to stimulate the cerebral nerve using induced power generated by magnetic induction; and
    the hat module including a magnetic field disk, wherein a plurality of magnets are attached to a surface of the magnetic field disk along a circumference thereof and the magnetic field disk is configured to spin along with the plurality of magnets to generate the rotating magnetic field.

2. The DBS device of claim 1, wherein the hat module comprises:
    the magnetic field disk for generating the rotating magnetic field toward the implantation module to thereby generate power required for driving the implantation module;
    an electric motor for rotating the magnetic field disk to thereby generate the rotating magnetic field; and
    a controller for controlling the electric motor.

3. The DBS device of claim 1, wherein the implantation module comprises:

a stimulation pin configured to be implanted through the skull under the scalp to thereby contact a deep cerebral nerve and to provide an electric stimulation to the nervous system of the patient;

an induction coil plate which, when combined with the rotating magnetic field generated by the hat module, is configured to generate the induced power; and a power modulator for modulating the induced power generated by the induction coil plate into power for driving the stimulation pin.

4. The DBS device of claim 3, wherein the induction coil plate comprises:

the power modulator attached to a center of the induction coil plate; and an induction coil formed of a metal line in a predetermined pattern around the power modulator.

5. The DBS device of claim 3, wherein:

the hat module further comprises a controller and a transmitter configured to be controlled by the controller to transmit a nerve stimulation command signal; and the implantation module further comprises a receiver for receiving the nerve stimulation command signal from the transmitter and transmitting the nerve stimulation command signal to the power modulator.

* * * * *